United States Patent [19]

Knitsch et al.

[11] 4,134,943
[45] Jan. 16, 1979

[54] PRODUCTION OF POROUS TABLETS

[75] Inventors: Karl-Wolfgang Knitsch, Starnberg; Alexander Hagen, Tutzing; Eberhard Munz, Polling; Helmut Determann, Starnberg, all of Germany

[73] Assignee: Boehringer Mannheim GmbH, Mannheim-Waldhof, Germany

[21] Appl. No.: 747,263

[22] Filed: Dec. 3, 1976

[30] Foreign Application Priority Data

Dec. 16, 1975 [DE] Fed. Rep. of Germany ....... 2556561

[51] Int. Cl.$^2$ ............................................. A61J 3/10
[52] U.S. Cl. .......................................... 264/28; 8/79; 264/49; 264/101; 264/140; 424/14
[58] Field of Search .................. 8/79; 424/14; 264/28, 264/49, 101, 102, 140

[56] References Cited

U.S. PATENT DOCUMENTS

| 2,877,159 | 3/1959 | Lachman | 264/101 |
| 3,607,753 | 9/1971 | Suchoff | 264/28 |
| 3,789,119 | 1/1974 | Fusari | 264/117 |
| 3,812,224 | 5/1974 | Smith | 264/101 |
| 3,885,026 | 5/1975 | Heinemann | 424/14 |

Primary Examiner—Paul R. Michl
Attorney, Agent, or Firm—Sprung, Felfe, Horn, Lynch & Kramer

[57] ABSTRACT

Porous tablets are produced by mixing the tablet components with a liquid solvent which is inert towards the components of the tablet and which freezes at a temperature from about −30 to +25° C, the solvent constituting about 5 to 80% by weight of the total mixture, introducing the mixture into an inert cooling medium at a temperature low enough to solidify the solvent, pressing the mixture including the solidified solvent into tablets at a temperature below the freezing point of the solvent, and then evaporating the solvent from the tablets. Advantageously the solvent is water, cyclohexane, benzene and/or tert.-butanol, optionally containing alcohol. The tablets readily disintegrate in liquid.

10 Claims, No Drawings

PRODUCTION OF POROUS TABLETS

The present invention is concerned with a new process for the production of porous tablets, which is a further development of the process described and claimed in U.S. Pat. No. 3,885,026.

Because of the case of handling and the simplicity of dosing, not only pharmaceutical tablets but also reagent tablets for diagonostic and analytical purposes are used to an ever increasing extent. However, most active materials and reagents cannot be tabletted by themselves since they form hard tablets which do not readily disintegrate and, in addition, in many cases, they tend to stick to the presses used.

Tablets which disintegrate quickly are only obtained by the addition of disintegration agents, such as carboxymethyl-cellulose, starch or the like, filling materials, such as lactose, phosphates or the like, and lubricating agents; such as talc, stearic acid, paraffin or the like. Whereas it is easy to find appropriate, physiologically compatible adjuvants for pharmaceuticals, reagent tablets, which are generally required to give optically clear solutions, cannot be produced in this way or can only be produced with difficulty. In particular, the conventionally used lubricating agents which are intended to prevent adherence of the tablet masses to the presses are nearly all insoluble in water. Therefore, it has been proposed to press sticky reagents together with very large amounts of readily tablettable filling agents or to employ high pressures for the pressing. However, both processes are unsatisfactory since tablets are formed which are either unnecessarily large or which are too hard and do not readily disintegrate.

Another known process gives the so-called "molded tablets". In this case, the tablet components are pasted with water or with an organic solvent, in which at least one of the components partially dissolves, to give a stiff slurry which can be formed into tablets in special machines whereafter the tablets are carefully dried. Upon evaporation of the solvent, the substances dissolved therein stick together with undissolved particles, whereby the tablets receive their strength. Due to the evaporation of the solvent, fine hollow spaces remain behind into which solvent can penetrate upon dissolving again. Although these tablets are satisfactory from the point of view of their rate of dissolution, they are, because of the practically pressureless method of production used, frequently too soft and brittle so that difficulties arise in packing and transporting. Furthermore, the utilization of this process is limited due to the fact that many reagents, especially enzymes and indicators, are damaged by organic solvents and, in addition, vapors of organic solvents make necessary the provision of special safety measures in the production of the tablets. Furthermore, water cannot be used as solvent for very readily water-soluble materials, i.e. for most reagent tablets.

According to U.S. Pat. No. 3,885,026, there is provided a process for the production of porous tablets, wherein the components of the tablets are hard pressed together with an inert, solid adjuvant which sublimes at a temperature which does not adversely affect any of the tablet components, whereafter the adjuvant is sublimed. Due to the hard pressing on normal tabletting machines, tablets are formed with a great mechanical stability and, at the same time, the addition of lubricants of low solubility is unnecessary. Since these pressed tablets, in contradistinction to "molded tablets", are form stable, they do not shrink up upon removal of the adjuvant so that when the adjuvant is sublimed out, comparatively large hollow spaces and canals are left behind through which solvents can penetrate. As adjuvants according to U.S. Pat. No. 3,885,026 there are used readily sublimable materials or materials which are readily converted into gaseous decomposition products, which materials are readily tablettable and do not react with the other components of the tablets. As examples of such materials, there are mentioned urethane, urea, ammonium bicarbonate, hexamethylenetetramine, benzoic acid, phthalic anhydride, naphthalene and camphor.

Although, according to the process of U.S. Pat. No. 3,885,026 sufficiently hard and rapidly dissolving tablets are obtained, we have found it to be disadvantageous that the last residues of the adjuvants can only be removed slowly or at comparatively high temperatures and that these adjuvants can have a negative influence on the activity of some sensitive enzymes.

Therefore, the problem exists of finding adjuvants which are easier to remove. There is also the problem of finding adjuvants which do not have a deleterious effect on extremely sensitive materials and are, therefore, of more generally applicability.

Surprisingly, we have found that materials which are liquid at ambient temperature, such as water or cyclohexane, and which have hitherto only been used as materials for forming hollow spaces in the laborious and unsatisfactory production of "molded tablets", can also be used for the production of pressed and thus form-stablized tablets according to the proess of U.S. Pat. No. 3,885,026.

Thus, according to the present invention, there is provided a process for the production of porous tablets, wherein the tablet components are mixed with a solvent which is inert towards the components of the tablet and which freezes at a temperature of about $-30$ to $+25°$ C., the so vent constituting about 5 to 80% by weight of the total mixture the mixture is solidified by introduction into an inert cooling medium, pressed into tabelts at a temperature below the freezing point of the solvent and the solvent then evaporated.

The materials to be tabletted are either worked up to a stiff slurry with an amount of solvent sufficient for the necessary pore formation or, in the case of comparatively large amounts of solvent or in the case of a better solubility of the materials to be tabletted, are worked up to give a solution. This slurry or solution is divided up into small particles or droplets and introduced into an inert cooling medium, the solvent and the active materials thereby separating into crystalline phases. If the solvent is only present in low concentration, the stiff slurry can be pressed through a sieve of appropriate mesh size and the resultant granules allowed to fall into a cooling medium. When the mixture is of low viscosity or is a solution, it can be sprayed through nozzles or spray cannules and introduced into a cooling medium im the form of fine droplets. In both cases, after separation from the cooling medium, flowable granulates are obtained which can be pressed in the usual manner in tablet presses to give tablets of the desired shape and size. Of course, care is to be taken that the pressing process is carried out at a temperature below the melting point of the eutectic mixtures of the tablet components with the solvent. The solvent can be removed from the finished tablets, for example by lyophilization or also by air drying when the tablets obtained are sufficiently form-stable even after the solvent has melted.

The rate of dissolution of tablets obtained according to this process can be controlled within wide limits, especially by the amount of solvent added and by the size and number of the hollow spaces left behind after the evaporation thereof. Naturally, the hardness of the tablets is the greater, the smaller is the amount of solvent added and, therefore, the smaller the number and size of the hollow spaces. Furthermore, the hardness is also considerably influenced by the pressure used for the pressing, the tablets being harder, the more strongly the components are compressed and compacted together. Pressures of about 500 to 5000 kp/cm$^2$ are normally employed. Furthermore, it is possible to select solvents in which at least one of the substances to be tabletted is soluble so that this substance is dissolved either by the localized heating resulting upon pressing or by melting after the pressing process and subsequently, upon decompressing or upon drying, the mixture sticks together and thus the hardness of the resulting tablets is increased. On the other hand, of course, especially porous tablets can be obtained by carrying out the production of the tablets under very low pressures and removing the solvent by lyophilization at a low temperature, as well as by using comparatively large amounts of solvents, which increases the number and size of the hollow spaces.

Surprisingly, by means of this process, it is also possible to tablet salts which are completely soluble in the solvent and, in particular, these mixtures can also be satisfactorily tabletted without the addition of lubricants without sticking to the press, this process thereby differing especially advantageously from that used for the production of "molded tablets".

As solvents, there can, in principle, be used all those which, at ambient temperature, do not damage the components of the tablets, which freeze upon cooling in technically useable ranges, i.e. about +25° C down to about −30° C even in the presence of the tablet components and preferably with phase separation and which can be easily evaporated or sublimed. Because of their universal applicability and cheapness, it is especially preferred to use water, cyclohexane, benzene or tert.-butanol, as well as mixtures thereof or mixtures thereof with lower alcohols.

The amount of solvent used depends upon the particular requirements for the tablet hardness and the disintegration time and is from about 5 to 80%, referred to the total weight of the mixture. For the production of relatively firm tablets which are, however, form-stable and can be dried at ambient temperature, there is generally used a slurry of active materials containing about 5 to 25% by weight of solvent and for the production of soft but rapidly dissolving tablets, there is used a solution of the active materials containing about 30 to 80% by weight and preferably about 30 to 50% by weight of solvent.

The tablets produced by the process according to the present invention disintegrate within a few seconds into small particles which can also be dissolved in less than one minute. The rate of dissolution of these tablets is, therefore, superior to that of the tablets produced by the process according to U.S. Pat. No. 3,885,026.

The following Examples are given for the purpose of illustrating the present invention:

EXAMPLE 1

Sodium chloride tablets 99.5 parts by weight of sodium chloride are finely ground and well mixed with 0.5 parts by weight of polyvinyl-pyrrolidone. The mixture is pasted with 20% by weight of dimineralized water and granulated by passing through a sieve with a mesh size of 0.8 mm into liquid nitrogen. The frozen, flowable granulate obtained is pressed into tablets at −20 to −25° C using a pre-cooled tabletting press, at a pressure of 3000 kp/cm$^2$. The tablets obtained are dried at ambient temperature over a drying agent.

tablet size: diameter 6 mm height 2.5 mm
tablet weight: 88 – 90 mg
tablet hardness: less than 0.5 kg Stoke's hardness
solubility in 1 ml water: 17 seconds.

EXAMPLE 2

Albumin tablets 0.5 part by weight albumin, 0.5 part by weight polyvinyl pyrrolidone, 5.0 parts by weight sodium chloride and 94.0 parts by weight mannitol are well mixed together, pasted with 40% by weight of cyclohexane and granulated by passing through a sieve with a mesh size of 0.8 mm into liquid nitrogen. The frozen, flowable granulate obtained is tabletted at −20 to −25° C in a pre-cooled tabletting press as in Example 1. The tablets obtained are air dried at ambient temperature under a flue.

tablet size: diameter 6 mm height 4 mm
tablet weight: 98 – 99 mg
tablet hardness: less than 0.5 kg Stoke's hardness
solubility in 1 ml. water: 14 seconds

EXAMPLE 3

Glutamate-oxalacetate-transaminase tablets 1.86 parts by weight sodium ethylenediamine-tetraacetate, 2.42 parts by weight tris-(hydroxymethyl)-aminomethane, 26.62 parts by weight L-aspartic acid, 14.34 parts by weight anhydrous sodium carbonate, 0.15 parts by weight nicotinamide-adenine-dinucleotide (reduced, disodium salt (NADH-Na$_2$)), 2 parts by weight (4000 U) lactate dehydrogenase (lyophilizate), 2 parts by weight (1000 U) malate dehydrogenase (lyophilizate), 0.25 parts by weight polyvinyl-pyrrolidone, 1.50 parts by weight Polywax 5/6000 and 48.86 parts by weight mannitol are well mixed together pasted with 50% by weight of a mixture of cyclohexane/ethanol (85:15 v/v) and granulated by passing through a sieve with a mesh size of 0.8 mm directly into liquid nitrogen. The frozen, flowable granulate obtained is tabletted as in Example 1. The tablets obtained are dried by lyophilization.

tablet size: diameter 5 mm; height 2.5 mm
tablet weight: 34 – 35 mg
tablet hardness; less than 0.5 kg Stokes' hardness
solubility in 1 ml. water: 10 seconds.

EXAMPLE 4

Sodium chloride-mannitol tablets 10 parts by weight sodium chloride, 7.5 parts by weight mannitol, 8.0 parts by weight Polywax 5/6000, 2.5 parts by weight Kollidon VA 64 and 2.0 parts by weight sodium alginate are dissolved in warm water and sprayed in the form of a 30% solution, at a pressure of 3.0 atmospheres, through an injection needle (No. 12) into liquid nitrogen. The frozen, readily flowable granulate obtained, with a water content of 70% by weight, is tabletted in the form of ice at −20 to −25° C in a pre-cooled tabletting press. The granulate can be pressed without any melting effect or sticking taking place. The tablets obtained are dried in a desiccator over a drying agent or by lyophilization.

tablet size: diameter 12 mm ; height 5.5 mm
tablet weight: 25 - 27 mg
tablet hardnes: less than 0.5 kg Stokes' hardness
disintegration time in 1 ml. water: 6 seconds
solubility in 1 ml. water: 25 seconds.

EXAMPLE 5

Alkaline phosphatase test tablets 5.75 parts by weight p-nitrophenyl phosphate di-TRIS salt, 50.00 parts by weight sodium chloride, 2.70 parts by weight Polywax 4000, 0.27 parts by weight Kollidon VA 64 and 31.28 parts by weight mannitol are well mixed together, pasted with 40% by weight cyclohexane and granulated by passing through a granulation sieve with a mesh size of 6 mm , directly into liquid nitrogen. The frozen, flowable granulate obtained is tabletted as in Example 1. The tablets obtained are dried at ambient temperature under waterpump vacuum.

tablet size: diameter 6 mm ; height 2.5 mm
tablet weight: 90 mg
tablet hardness: less than 0.5 kg Stokes' hardness
solubility in 1 ml. water: 12 seconds

EXAMPLE 6

Urease tablets 5.20 parts by weight urease lyophilisate (2.7 U/tablet), 3.00 parts by weight sodium chloride, 60.00 parts by weight sorbitol, 15.0 parts by weight sorbitol, 1.50 parts by weight Polywax 4000 and 0.30 parts by weight Kollidon VA 64 are well mixed together, pasted with 30% by weight cyclohexane and granulated by passing through a granulation sieve with a mesh size of 6 mm. directly into liquid nitrogen. The frozen, flowable granulate obtained is tabletted as in Example 1. The tablets obtained are dried under a vacuum of about 60 mm Hg.

tablet size: diameter 6 mm ; height 2.3 mm
tablet weight: 70 mg
tabelet hardness: less than 0.5 kg Stokes' hardness
solubility in 1 ml. water: 14 seconds Throughout the foregoing examples the weight % of added solvent has reference to the weight of mixture plus solvent.

It will be appreciated that the specification and examples are illustrative but not limitative of the present invention and that other embodiments within the spirit and scope of the invention will suggest themselves to those skilled in the art.

What we claim is:

1. A process for the production of porous tablets which are readily soluble in aqueous solutions, comprising mixing the tablet components which are readily soluble in aqueous solutions with a liquid solvent which is inert towards the components of the tablet and which freezes at a temperature from about −30 to +25° C, the solvent constituting about 5 to 80% by weight of the total mixture, introducing the mixture into an inert cooling medium at a temperature low enough to solidify the solvent, pressing the mixture including the solidified solvent into tablets at a temperature below the freezing point of the solvent, and then evaporating the solvent from the tablets.

2. The process according to claim 1, wherein the solvent used comprises at least one of water, cyclohexane, benzene and tert.-butanol.

3. The process according to claim 2, wherein the solvent includes a lower alcohol.

4. The process according to claim 1, wherein the solvent is evaporated by lyophilization.

5. The process according to claim 1, wherein the solvent is evaporated by warming the tablets to ambient temperature and then drying in air.

6. The process according to claim 1, wherein the tablets are pressed at a pressure of about 500 to 5000 kp/cm$^2$.

7. The process according to claim 1, wherein about 5 to 25% by weight of solvent is used based on the total weight of solvent plus mixture, the resulting tablets being relatively hard.

8. The process according to claim 1, wherein about 30 to 80% by weight of solvents is used based on the total weight of solvent plus mixture, the resulting tablets being relatively soft.

9. The process according to claim 8, whereina about 30 to 50% by weight of solvent is used.

10. The process according to claim 6, wherein the solvent used comprises at least one of water, cyclohexane, benzene and tert.-butanol optionally mixed with a lower alcohol, the solvent being used in about 5 to 80% by weight of solvent plus mixture.

* * * * *